(12) United States Patent
Bavouzet et al.

(10) Patent No.: US 10,106,823 B2
(45) Date of Patent: Oct. 23, 2018

(54) YEAST STRAINS FOR PRODUCING FIRST-GENERATION ETHANOL

(71) Applicant: LESAFFRE ET COMPAGNIE, Paris (FR)

(72) Inventors: Jean-Michel Bavouzet, Compiégne (FR); Anne-Dominique Quipourt, Marc en Baroeul (FR); Annie Tbaikhi, Wambrechies (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 15/104,572

(22) PCT Filed: Dec. 30, 2014

(86) PCT No.: PCT/FR2014/053575
§ 371 (c)(1),
(2) Date: Jun. 15, 2016

(87) PCT Pub. No.: WO2015/101753
PCT Pub. Date: Jul. 9, 2015

(65) Prior Publication Data
US 2016/0312245 A1 Oct. 27, 2016

(30) Foreign Application Priority Data
Dec. 30, 2013 (FR) .................................. 13 63672

(51) Int. Cl.
C12P 7/06 (2006.01)
C12R 1/865 (2006.01)
C12P 7/08 (2006.01)

(52) U.S. Cl.
CPC .................................... *C12P 7/06* (2013.01); *C12P 7/08* (2013.01); *C12R 1/865* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 4,334,026 A | * | 6/1982 | Chynoweth | C02F 3/28 127/37 |
| 6,140,108 A | | 10/2000 | Mortimer et al. | |
| 9,175,257 B2 | | 11/2015 | Colavizza et al. | |
| 2011/0129901 A1 | * | 6/2011 | Fuentes | C07K 14/395 435/247 |
| 2011/0165612 A1 | | 7/2011 | Colavizza et al. | |
| 2013/0052709 A1 | | 2/2013 | Wietgrefe et al. | |

FOREIGN PATENT DOCUMENTS

| | | |
|---|---|---|
| WO | 98/31784 | 7/1998 |
| WO | 2010/031916 | 3/2010 |
| WO | 2011/100272 | 8/2011 |

OTHER PUBLICATIONS

International Search Report and Written Opinion of the International Searching Authority dated Feb. 26, 2015, which issued during prosecution of International Application No. PCT/FR2014/053575.
Basso, et al. "Yeast selection for fuel ethanol production in Brazil" FEMS Yeast Research, Aug. 2008, 8(7):1155-1163.

* cited by examiner

*Primary Examiner* — Jennifer M. H. Tichy
(74) *Attorney, Agent, or Firm* — Duane Morris LLP; Thomas J. Kowalski; Deborah L. Lu

(57) ABSTRACT

The present invention concerns yeast strains that have improved properties relative to the specialized strains that are used in the production of first-generation ethanol. In particular, the strains of the invention have an increased ethanol yield, a lower production of glycerol and ethanol production kinetics that are similar or slightly slower than standard strain D1B. The present invention also concerns the yeasts obtained by culturing said strains, and the use of said yeasts and/or of said strains in the industrial production of ethanol.

6 Claims, 3 Drawing Sheets

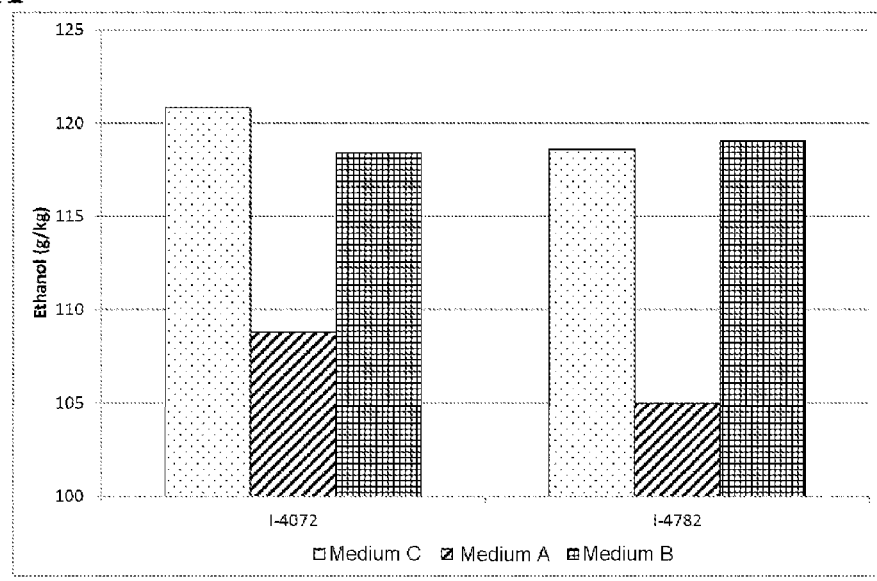
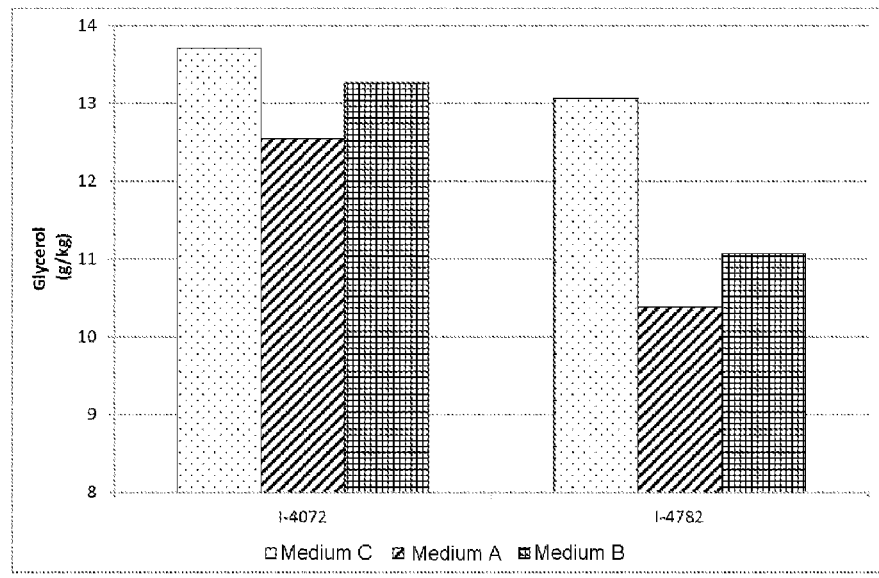
Figure 1(A)-(B)

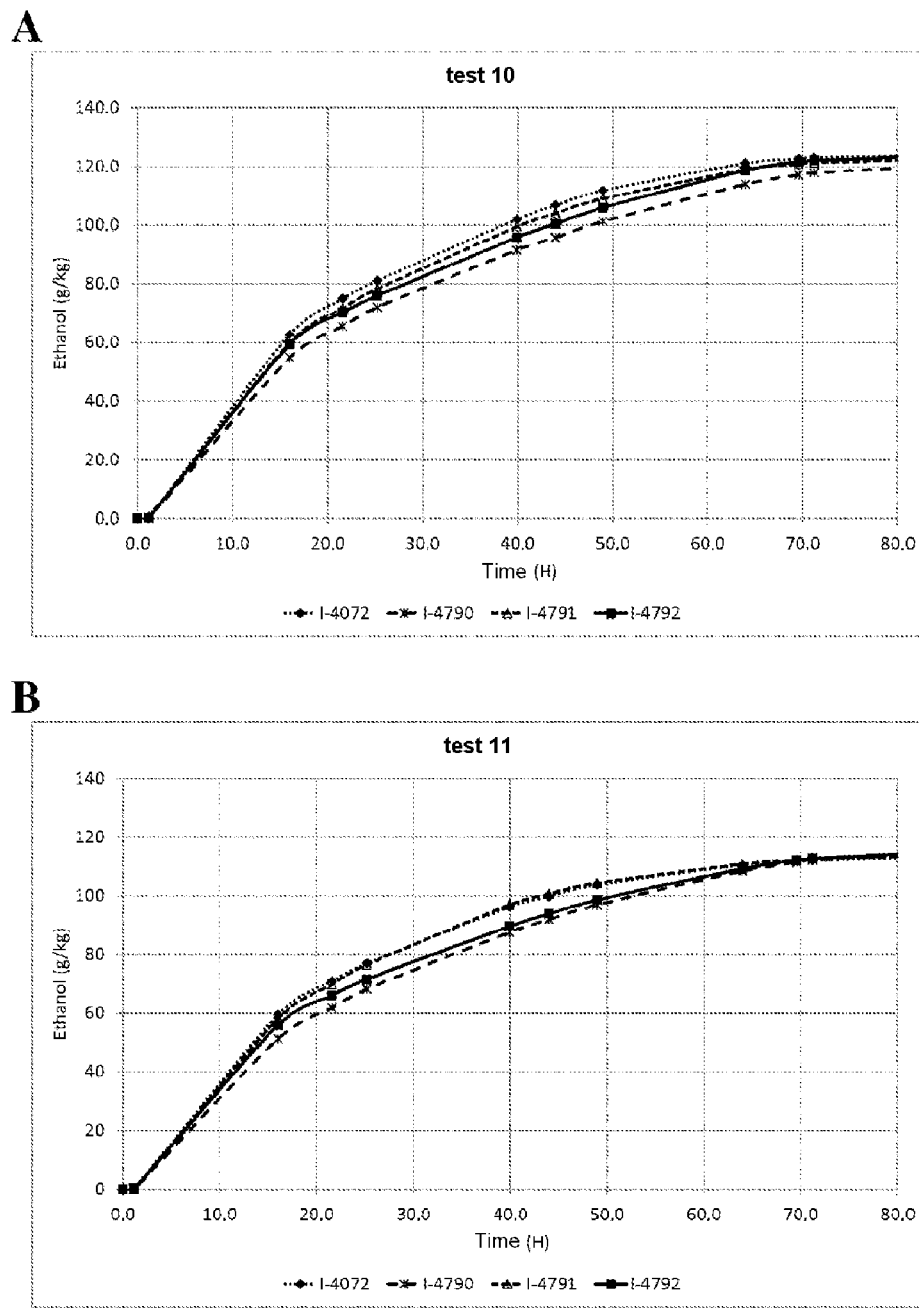
Figure 2(A)-(B)

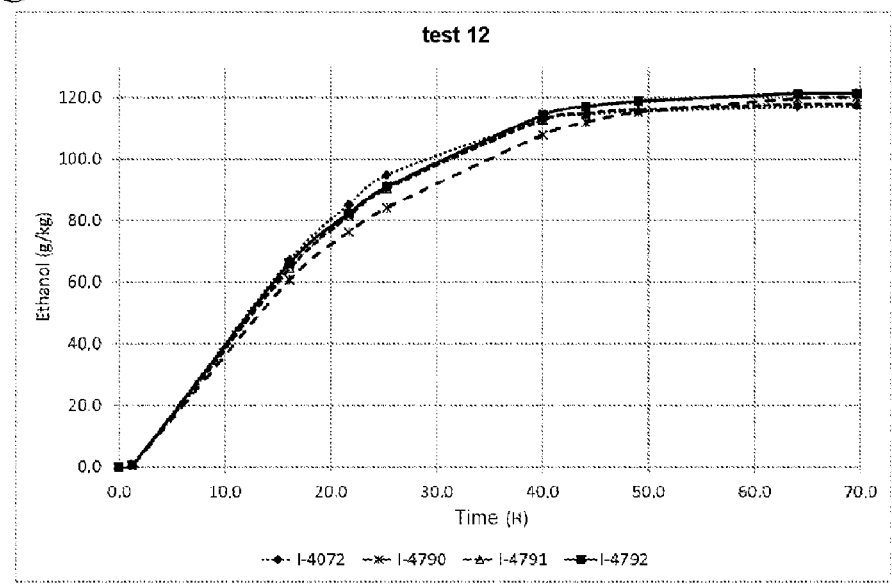
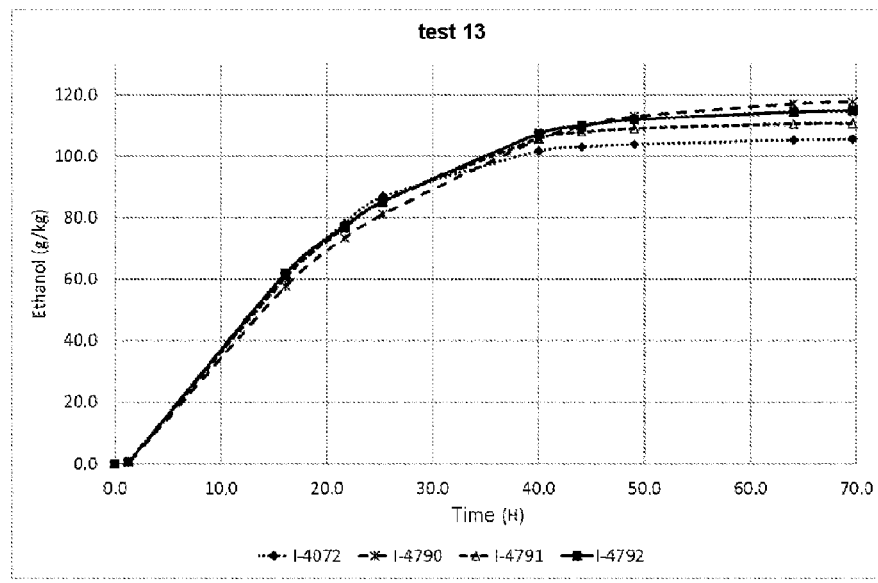
Figure 2(C)-(D)

YEAST STRAINS FOR PRODUCING FIRST-GENERATION ETHANOL

RELATED APPLICATIONS AND INCORPORATION BY REFERENCE

The present patent application is filed pursuant to 35 U.S.C. § 371 as a U.S. National Phase application of International Patent Application No. PCT/FR2014/053575, which was filed on Dec. 30, 2014, claiming the benefit of priority to French patent application number FR 13 63 672 filed on Dec. 20, 2013. The content of each of the aforementioned patent applications is incorporated herein by reference in its entirety.

FIELD OF THE INVENTION

The present invention relates to yeast strains which produce first-generation ethanol, to yeasts obtained by culturing these strains, and to processes for industrial production of ethanol from said yeasts. More especially, the present invention relates to three specific strains which exhibit a strong tolerance to ethanol, a lower production of glycerol than the most effective strains currently used in ethanol production processes, and a high ethanol yield. The strains of the invention also have fast ethanol production kinetics.

CONTEXT OF THE INVENTION

The decrease in non-renewable energy resources and the growing concern in the face of the increase in greenhouse gas emissions are responsible for the need to find energy sources that are alternatives to fossil fuels (oil, coal, gas). Plant biomass from forests and/or from agricultural or food-processing products and/or coproducts constitutes a considerable source of carbon for the production of molecules of industrial interest. The ethanol produced from the fermentable sugars contained in plants is used in vehicles which have combustion engines. Thus, bioethanol production has experienced a rapid development over the past few years in North America and in Europe. In 2008, more than 56 billion liters of ethanol were produced worldwide from plant biomass.

First-generation bioethanol is produced by fermentation of hexoses (sugars comprising six carbons) contained in biomasses rich in starch (grains of corn, barley, wheat, cassava, potato tubers, etc.) or in sucrose (sugar cane, sugar beet, sweet sorghum, etc.), whereas "second-generation" bioethanol is produced by conversion of cellulose and of hemicellulose contained in agricultural residues such as cereal straws or corn stover, forest residues, wood, energy crops such as switchgrass or copses with a short or very short rotation (poplar for example).

The processes for obtaining the fermentation media rich in sugars of first-generation processes are relatively simple and well controlled. In the case of sweet plants such as sugar cane, sweet sorghum or sugar beet, the plant is ground or cut into pieces and a sugary juice is obtained directly or after soaking in water. The alcoholic fermentation can be carried out using the crude juice obtained, using the concentrated juice or using concentrated juices such as molasses obtained after extraction of a fraction of the sugars initially present. In the case of starch-rich plant fractions such as corn grains, the starch must first be hydrolyzed to glucose so that the yeast can then convert to ethanol. The standard hydrolysis process consists of a first phase during which the starch chains are converted to shorter chains by the action of an alpha-amylase, followed by an "SSF" (simultaneous saccharification and fermentation) fermentation step during which the dextrins are hydrolyzed by adding glucosidases and during which the glucose is fermented to ethanol by the yeast. Some processes, termed cold processes, perform a reduced starch hydrolysis, or even no starch hydrolysis, before the fermentation step. In the case of second-generation ethanol produced from lignocellulosic material, the chemical and enzymatic hydrolysis processes are much more complex and laborious since the lignocellulosic material is made up of a rigid matrix that is difficult to destructure in order to release the cellulose and the hemicellulose from the lignin. The hydrolysis of lignocellulosic materials generates hydrolyzates containing hexoses and/or pentoses. Whatever the biomass used or the product employed, the final product is the same, only the production process differs.

In Europe, sugar beet and cereals (wheat, barley, corn) are the main resources used for the production of ethanol of agricultural origin. The sugars (glucose, fructose or sucrose) contained in sweet plants (sugar beet, sugar cane) and starchy plants (cereals such as wheat or corn) are converted into alcohol by an industrial fermentation process using yeasts. The alcohol is then distilled and dehydrated so as to obtain bioethanol. The coproducts obtained during the production process (spent grains and pulps) are intended for animal feed.

The yeasts used by producers of first-generation ethanol are principally specialized yeasts which make it possible to optimize the profitability of the production process. These yeasts are, inter alia: Ethanol Red® (Fermentis®), Thermosacc® (Lallemand®), Angel Super Alcohol® (Angel®) and Fali® (AB Mauri®). The expected qualities of these yeasts are their ability to rapidly produce high concentrations of ethanol and to exhaust the sugars of fermentation media over the temperature and pH ranges representative of industrial conditions. These qualities are particularly sought in processes using cereals, corn in particular, which generate hydrolyzates with high sugar concentrations. Indeed, producers adjust the sugar content of their fermentation medium so that it is as high as possible while at the same time ensuring that the sugar is converted to ethanol as rapidly and as completely as possible. Just as the producers want the yeast to convert all of the sugars of the medium to ethanol, they also want the overall yield of conversion of the consumed sugars to ethanol to be as high as possible and, consequently, the fewest coproducts such as glycerol to be generated during the fermentation.

Having a yeast exhibiting better tolerance to ethanol and having a yeast producing less glycerol while at the same time ensuring a productivity in terms of volume that is equivalent or greater both under usual fermentation conditions and during fluctuations in fermentation parameters would allow ethanol producers to increase the profitability of their facility by increasing ethanol production. There is therefore still a need to have new improved yeast strains for the production of first-generation ethanol.

SUMMARY OF THE INVENTION

The present invention relates to *Saccharomyces cerevisiae* yeast strains which have improved properties compared with the specialized yeast strains commonly used in the production of first-generation ethanol.

Thus, in particular, a subject of the present invention is the *Saccharomyces cerevisiae* yeast strain 53-137 that was deposited on Jul. 25, 2013, at the CNCM (Collection Nationale de Cultures de Micro-organismes [French National Collection of Microorganism Cultures] of the Institut Pasteur, 25 rue du Docteur Roux, 75724 Paris, Cedex 15) under number I-4791 under the conditions of the treaty of Budapest.

Another subject of the present invention is the *Saccharomyces cerevisiae* yeast strain 53-005 that was deposited on Jul. 25, 2013, at the CNCM (Collection Nationale de Cultures de Micro-organismes [French National Collection of Microorganism Cultures] of the Institut Pasteur, 25 rue du Docteur Roux, 75724 Paris, Cedex 15) under number I-4790 under the conditions of the treaty of Budapest.

Another subject of the present invention is the *Saccharomyces cerevisiae* yeast strain 53-214 that was deposited on Jul. 25, 2013, at the CNCM (Collection Nationale de Cultures de Micro-organismes [French National Collection of Microorganism Cultures] of the Institut Pasteur, 25 rue du Docteur Roux, 75724 Paris, Cedex 15) under number I-4792 under the conditions of the treaty of Budapest.

The present invention also relates to a yeast obtained by culturing a *Saccharomyces cerevisiae* yeast strain chosen from the *Saccharomyces* yeast strain that was deposited on Jul. 25, 2013, at the CNCM under number I-4791, the *Saccharomyces cerevisiae* yeast strain that was deposited on Jul. 25, 2013, at the CNCM under number I-4790 and the *Saccharomyces cerevisiae* yeast strain that was deposited on Jul. 25, 2013, at the CNCM under number I-4792.

A subject of the present invention is also the use of a *Saccharomyces cerevisiae* yeast strain chosen from the *Saccharomyces* yeast strain that was deposited on Jul. 25, 2013, at the CNCM under number I-4791, the *Saccharomyces cerevisiae* yeast strain that was deposited on Jul. 25, 2013, at the CNCM under number I-4790 and the *Saccharomyces cerevisiae* yeast strain that was deposited on Jul. 25, 2013, at the CNCM under number I-4792, or of a yeast obtained by culturing one of these strains, for the production of first-generation ethanol from biomass.

A subject of the present invention is also a method for producing first-generation ethanol from biomass, comprising a fermentation step using a *Saccharomyces cerevisiae* yeast strain chosen from the *Saccharomyces* yeast strain that was deposited on Jul. 25, 2013, at the CNCM under number I-4791, the *Saccharomyces cerevisiae* yeast strain that was deposited on Jul. 25, 2013, at the CNCM under number I-4790 and the *Saccharomyces cerevisiae* yeast strain that was deposited on Jul. 25, 2013, at the CNCM under number I-4792 or a yeast obtained by culturing one of these strains.

In some embodiments, the biomass is rich in sugar and/or starch and is chosen from, or originates in particular from, corn, wheat, barley, rye, sorghum, cassava, triticale, potato, sweet potato, sugar cane, sugar beet and sweet sorghum.

In some preferred embodiments, the biomass is chosen from or originates from corn, wheat, barley, cassava, sugar beet and sugar cane.

A subject of the present invention is also the production of spent grains and spent grains supplemented with soluble materials from the fermentation residues obtained during the ethanol production processes.

A more detailed description of some preferred embodiments of the invention is given below.

DEPOSITS

The Deposits with CNCM, under deposit accession numbers I-4782, I-4790, I-4791, and I-4792 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

As mentioned above, the present invention relates to three *Saccharomyces cerevisiae* yeast strains that are useful for the production of first-generation ethanol. The three strains of the invention were obtained by means of a hybridization and selection program. They result from hybridization between the *Saccharomyces cerevisiae* yeast strain deposited at the CNCM on Sep. 4, 2008, under number I-4072, a strain belonging to the applicant, and the *Saccharomyces cerevisiae* yeast clone deposited at the CNCM on Jun. 26, 2013, under number I-4782, which also belongs to the applicant.

The I-4072 yeast strain is a strain selected by the Applicant as having the strongest tolerance to ethanol among a panel of 21 evaluated strains.

The *Saccharomyces cerevisiae* yeast clone I-4782 was selected by the Applicant as having a tolerance to ethanol that is high although lower than that of the I-4072 strain, but as having a glycerol production lower than that of the I-4072 strain.

The hybrid selection program led to the three strains of the invention. Each of these strains constitutes an alternative to the most effective specialized strains which are currently used in the industrial production of first-generation ethanol. Indeed, the three strains of the invention have a higher tolerance to ethanol than the I-4072 reference strain and at the same time produce first-generation ethanol with a higher yield than the I-4072 strain owing to a lower production of glycerol, which is a by-product of the fermentation reaction. This good tolerance is observed whatever the temperature (32° C., 35° C. or 38° C.), the pH (4.0, 5.0 or 5.5) and the provision of inorganic nitrogen (150 to 500 ppm) during fermentation, which makes them strains that are particularly suitable for the production of first-generation ethanol where fluctuations in fermentation parameters are common. Furthermore, the strains of the invention have the advantage of having ethanol production kinetics that are similar or slightly lower than those of the I-4072 reference strain.

The invention also relates to a yeast obtained by culturing one of the strains of the invention. Processes for culturing a yeast strain are known in the art, and those skilled in the art know how to optimize the culture conditions for each strain depending on its nature.

The yeast strains of the invention and the yeasts obtained by culturing these strains are of use in the production of first-generation ethanol from biomass. The term "biomass" is intended to mean herein any organic matter of plant origin that can become an energy source after conversion. Preferably, in the context of the invention, the biomass is derived from agricultural or food-processing products and/or coproducts. In particular, the biomass is preferably rich in sucrose or in starch, and is chosen from, or is derived from, for example, corn, wheat, barley, rye, sorghum, cassava, triticale, potato, sweet potato, sugar cane, sugar beet and sweet sorghum.

In some preferred embodiments, the biomass is chosen from, or is derived from, corn, wheat, barley or cassava.

The methods for producing first-generation ethanol from biomass and the use of yeasts in the fermentation step are known in the art. The most common industrial method make use of physical, chemical and biochemical treatments which ultimately aim to allow the fermentation of sugars and to produce ethanol. Several variants of this method exist and are known to those skilled in the art. The yeast strains of the invention and the yeasts obtained by culturing these strains can be used in any method for producing first-generation ethanol.

The invention applies particularly to the production of ethanol as a fuel, but also to the production of ethanol for the food, chemical, pharmaceutical and cosmetic industries.

Unless they are otherwise defined, all the technical and scientific terms used in the specification have the same meaning as that commonly understood by one skilled in the field to which this invention belongs. Likewise, all the publications, patent applications, all the patents and any other references mentioned herein are incorporated by way of reference.

EXAMPLES

The examples below describe some embodiments of the present invention. However, it is understood that the examples and the figures are presented only by way of illustration and do not in any way limit the scope of the invention.

BRIEF DESCRIPTION OF THE DRAWINGS

FIGS. 1A-B: Final concentrations at the end of the fermentation tests carried out on liquefied fermentation media according to example 1. (A) Ethanol concentration and (B) glycerol concentration. The media A, B and C are described in table 1.

FIGS. 2A-D: Kinetics of ethanol production by the I-4072 strain (A) and the hybrids I-4790 (B), I-4791 (C) and I-4792 (D) under various fermentation conditions.

Example 1: Selection of the Parental Strains to Cross With the I-4072 Strain

A panel of 21 strains or clones was tested during alcoholic fermentation. The tests were carried out under simultaneous saccharification and fermentation (SSF) conditions with an excess of sugars relative to the capacities for conversion to ethanol of the strains. Firstly, synthetic media containing starch dextrins with or without addition of soluble materials from the distillation residues were used. Secondly, fermentation media prepared from corn flour, from fractions of the soluble materials, from distillation residues, and from process water in the proportions given in the table below were used. These various elements were obtained from a factory producing industrial ethanol according to a first-generation process. The corn flour-based mixture was liquefied using Liquozyme™ SCDS (Novozymes) at 85° C. for 3 hours after adjustment of the pH to 5.6. The dose at which Liquozyme™ was used was 0.8 ml/kg of flour used. Before inoculation, the initial pH was adjusted to 5.0 or 4.5; various concentrations of urea (300, 600 and 1000 ppm of nitrogen equivalent) were added as indicated in the following table. Spyrizyme Fuel Ultra™ (Novozymes) was added at the dose of 0.6 ml/kg of flour. The fermentation temperature was regulated at 32° C. The strains were propagated beforehand in a rich synthetic medium in 500 ml baffled flasks (microaerated propagation).

TABLE 1

| | Medium | | |
|---|---|---|---|
| | A | B | C |
| initial pH | pH 4.5 | pH 5.0 | pH 4.5 |
| Temperature (° C.) | 32 | 32 | 32 |
| Flour (g) | 362.5 | 362.5 | 362.5 |
| Soluble materials from distillation residues (g) | 300 | 250 | 300 |
| Urea (ppm) | 300 | 600 | 1000 |
| Process water | QS 1 kg | QS 1 kg | QS 1 kg |

Among the various strains tested, the strain deposited at the CNCM under number I-4072 was retained as being, among all the strains tested, the strain producing the most ethanol. Among the various strains tested, the I-4782 strain was retained as being a strain producing large amounts of ethanol, although less than I-4072, and as producing smaller amounts of glycerol than the I-4072 strain.

It is interesting to note that the ethanol production kinetics of the I-4782 clone are quite slow compared with those of the I-4072 strain. The final concentrations of ethanol and of glycerol that were obtained during the tests are shown in FIGS. 1A and 1B.

The objective was therefore to obtain, by hybridization, at least one hybrid having a tolerance to ethanol greater than that of the I-4072 strain, a lower glycerol production than that of the I-4072 strain, and ethanol production kinetics at least similar to those of the I-4072 strain.

Example 2: Obtaining New Hybrids

Once the parental strains had been selected, various technical steps resulting in the development of new strains by crossing were carried out, comprising:
    obtaining, by sporulation then germination, segregants of the two parent strains and characterizing their sex type,
    carrying out the crosses after establishment of crossing tables, and
    isolating and identifying the new hybrids.

Selecting the elite segregants of the I-4072 strain. Segregants of the I-4072 strain were generated and evaluated on the basis of their ethanol production. Then, on the basis of these results, 8 spores of "alpha" sex type and 12 spores of "a" sex type having the best alcohol performance levels were selected.

Carrying out crosses and obtaining new strains. In order to obtain new strains, several series of crosses were carried out between the segregants of I-4072 selected and randomly chosen segregants of I-4782.

Identifying new hybrids. New hybrids were identified by mating type PCR.

Numerous strains were thus created and validated at the end of the crosses carried out. Among the hybrids, I-4791, I-4790 and I-4792, which are subjects of the present application, particularly stand out, as indicated later.

Example 3: Selection of the New Hybrids

In order to be able to select the best hybrids among the 292 newly created strains, four levels of selection were developed. These selections are based on monitoring loss of mass of alcohol fermentation media after inoculation with the strains to be studied, compared with the I-4072 control, and measurement of the ethanol concentration, of the remaining glucose and of the glycerol produced after 72 hours of fermentation at various temperatures (35° C. and 38° C.). The fermentation media used were synthetic media containing a high glucose concentration, above the capacities for conversion to ethanol of the strains tested. The selection criteria are better loss-of-mass kinetics than the I-4072 strain and/or decreased glycerol production compared with the I-4072 strain. The loss of mass is an indirect indicator of the ethanol production by the yeasts according to the stoichiometric equation: 1 mol glucose→2 mol $CO_2$+2 mol ethanol which makes it possible to link globally the mass of loss of mass of the medium in the form of $CO_2$ produced and evaporated to the mass of ethanol produced.

In the end, out of 292 strains, 18 hybrids were selected, including the I-4790, I-4791 and I-4792 strains. These strains were chosen because they have the following characteristics:

hybrid I-4790: at temperatures of 35° C. and 38° C., for an ethanol production equivalent to that of the I-4072 strain, the glycerol production is decreased by 15 to 20%. The loss-of-mass kinetics are however lower than those of the I-4072 strain;

hybrid I-4791: at temperatures of 35° C. and 38° C., the ethanol production is increased by 3.5% compared with that of the I-4072 strain, the loss-of-mass kinetics are faster than those of the I-4072 strain, and the glycerol production is equivalent to that of the I-4072 strain;

hybrid I-4792: at temperatures of 35° C. and 38° C., the ethanol production is equivalent to that of I-4072 (with a slight improvement at 38° C.), the loss-of-mass kinetics are equivalent to those of I-4072, and the glycerol production is 7.5 to 8% lower compared with that of I-4072.

Example 4: Ethanol Production From Corn Flour by the Hybrids With Excess of Sugars in the Medium Tests were carried out in media based on corn flour and fraction of soluble materials from industrial distillation residues. The tests were carried out at various fermentation temperatures, with various additions of nitrogen and at various initial pH values. The characteristics that were studied are: the maximum tolerance of the strains to ethanol, the glycerol production and the ethanol production kinetics.

The losses of mass of the fermentation media were measured over time. Once stabilization of the loss of mass had been reached, sampling of the fermentation medium was carried out and an assay by HPLC of the ethanol and glycerol concentrations was carried out. The masses of ethanol and glycerol produced were calculated from the concentration measured and from the mass of fermentation must at the time of the sampling in order to carry out the assay and the initial concentration and mass values.

Protocol.

The fermentation media were prepared from corn flour, fractions of the soluble materials from distillation residues and process water. In order to simulate as closely as possible the industrial production conditions, these various elements were obtained from factories for producing industrial ethanol according to first-generation processes. The proportions of the three industrial components were: corn flour (36% w/w), fraction of the soluble materials from distillation residues (35% w/w) and process water (29% w/w). The mixture was liquefied using Liquozyme™ SCDS (Novozymes) at 85° C. for 3 hours after adjustment of the pH to 5.6. The Liquozyme™ dose used was 0.8 ml/kg of flour used. Before inoculation, the pH was adjusted to 5 or 4 (according to the table), and various concentrations of urea (150, 250 and 500 ppm of nitrogen equivalent) were added. Sprizyme Fuel Ultra™ (Novozymes) was added at the dose of 0.6 ml/kg of flour. The strains were propagated beforehand in a rich synthetic medium in 500 ml baffled flasks (microaerated propagation). A cream yeast was prepared from the propagation medium by centrifugation and resuspension of the centrifugation pellet in water. The solids content of the cream yeast was determined and the fermentation medium was inoculated with the cream so as to have a level of inoculation of 0.5 g of dry yeast equivalent/kg of medium.

Tests carried out. The following table presents the conditions of the fermentation tests carried out and of the strains used.

TABLE 2

Fermentation test conditions.

| | Tests | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Conditions | | | | | | | | | | | | | | | |
| Medium | A | A | A | A | A | A | B | B | B | B | B | B | B | B | B |
| T (° C.) | 32 | 35 | 38 | 35 | 35 | 35 | 35 | 35 | 35 | 32 | 32 | 35 | 35 | 38 | 38 |
| N (ppm) | 500 | 500 | 500 | 150 | 250 | 500 | 150 | 250 | 500 | 500 | 500 | 500 | 500 | 500 | 500 |
| pH | 5 | 5 | 5 | 5 | 5 | 5 | 5 | 5 | 5 | 5 | 4 | 5 | 4 | 5 | 4 |
| Strains tested | | | | | | | | | | | | | | | |
| I-4072 | x | x | x | x | x | x | x | x | x | x | x | x | x | x | x |
| I-4790 | x | x | x | x | x | x | x | x | x | x | x | x | x | x | x |
| I-4791 | x | x | x | x | x | x | x | x | x | x | x | x | x | x | x |
| I-4792 | | | | | | x | | | x | x | x | x | x | x | x |

A: 36% corn flour, 35% soluble materials from distillation residues, 29% process water
B: 36% corn flour, 35% soluble materials from distillation residues, 29% process water
N: provision of nitrogen Results. The results obtained are presented in the tables below.

Tables 3 to 4. Final concentrations of ethanol and of glycerol and masses of ethanol and of glycerol produced in tests 1-9.

TABLE 3

| Strain | Final concentrations (g/kg) | | | Mass produced (g/kg of medium used) | |
|---|---|---|---|---|---|
| | Equiv. glucose | Glycerol | Ethanol | Glycerol | Ethanol |
| Test 1: 32° C., 500 ppm N, pH 5 | | | | | |
| I-4072 | 40.9 | 7.9 | 121.3 | 5.3 | 107.6 |
| I-4790 | 35.4 | 7.5 | 123.9 | 4.8 | 109.3 |
| I-4791 | 37.1 | 8.4 | 129.6 | 5.7 | 114.8 |
| Test 2: 35° C., 500 ppm N, pH 5 | | | | | |
| I-4072 | 37.7 | 6.7 | 110.5 | 5.0 | 98.9 |
| I-4790 | 28.7 | 6.2 | 116.4 | 4.5 | 103.8 |
| I-4791 | 32.7 | 6.5 | 111.5 | 4.8 | 99.7 |
| Test 3: 38° C., 500 ppm N, pH 5 | | | | | |
| I-4072 | 75.6 | 6.4 | 90.3 | 4.8 | 82.3 |
| I-4790 | 74.0 | 5.5 | 93.5 | 4.0 | 85.2 |
| I-4791 | 72.1 | 6.3 | 93.4 | 4.6 | 85.0 |
| Test 4: 150 ppm N, 35° C., pH 5 | | | | | |
| I-4072 | 46.2 | 15.9 | 109.9 | 8.5 | 98.6 |
| I-4790 | 26.6 | 14.8 | 116.1 | 7.4 | 103.4 |
| I-4791 | 34.4 | 15.5 | 113.5 | 8.1 | 101.3 |
| Test 5: 250 ppm N, 35° C., pH 5 | | | | | |
| I-4072 | 27.9 | 15.9 | 108.2 | 8.5 | 96.4 |
| I-4790 | 20.5 | 15.3 | 117.7 | 7.9 | 104.4 |
| I-4791 | 26.6 | 15.3 | 112.3 | 8.0 | 99.8 |
| Test 6: 500 ppm N, 35° C., pH 5 | | | | | |
| I-4072 | 15.9 | 15.7 | 117.4 | 8.3 | 104.2 |
| I-4790 | 11.4 | 14.8 | 122.0 | 7.4 | 108.0 |
| I-4791 | 16.0 | 15.0 | 119.9 | 7.7 | 106.4 |
| I-4792 | 11.2 | 15.4 | 122.4 | 8.0 | 108.4 |
| Test 7: 150 ppm N, 35° C., pH 5 | | | | | |
| I-4072 | 27.8 | 15.9 | 103.9 | 9.0 | 93.4 |
| I-4790 | 17.1 | 15.2 | 111.1 | 7.9 | 99.5 |
| I-4791 | 23.1 | 15.9 | 108.2 | 8.6 | 97.1 |
| Test 8: 250 ppm N, 35° C., pH 5 | | | | | |
| I-4072 | 35.2 | 16.3 | 114.9 | 9.0 | 102.6 |
| I-4790 | 22.6 | 15.5 | 122.1 | 8.1 | 108.4 |
| I-4791 | 30.6 | 15.2 | 117.5 | 7.9 | 104.6 |
| Test 9: 500 ppm N, 35° C., pH 5 | | | | | |
| I-4072 | 28.4 | 15.8 | 123.2 | 8.2 | 109.2 |
| I-4790 | 18.6 | 15.3 | 128.1 | 7.7 | 113.3 |
| I-4791 | 22.5 | 14.8 | 122.5 | 7.4 | 108.6 |
| I-4792 | 17.3 | 15.1 | 125.5 | 7.6 | 111.0 |

TABLE 4

| Strain | Final concentrations (g/kg) | | | Mass produced (g/kg of medium used) | |
|---|---|---|---|---|---|
| | Equiv. glucose | Glycerol | Ethanol | Glycerol | Ethanol |
| Test 11: 32° C., 500 ppm N, pH 4 | | | | | |
| I-4072 | 35.4 | 15.0 | 117.1 | 13.4 | 104.2 |
| I-4790 | 27.0 | 14.4 | 122.9 | 12.8 | 109.0 |
| I-4791 | 35.5 | 14.6 | 117.7 | 13.0 | 104.9 |
| I-4792 | 26.9 | 14.4 | 122.9 | 12.7 | 108.9 |
| Test 10: 32° C., 500 ppm N, pH 5 | | | | | |
| I-4072 | 18.5 | 16.2 | 127.3 | 14.3 | 112.2 |
| I-4790 | 16.2 | 15.1 | 129.5 | 13.3 | 114.1 |
| I-4791 | 22.5 | 15.5 | 126.2 | 13.7 | 111.3 |
| I-4792 | 15.3 | 15.3 | 130.3 | 13.4 | 114.6 |
| Test 13: 35° C., 500 ppm N, pH 4 | | | | | |
| I-4072 | 46.4 | 15.1 | 105.5 | 13.6 | 94.7 |
| I-4790 | 33.8 | 14.5 | 117.6 | 12.9 | 104.7 |
| I-4791 | 46.0 | 14.8 | 110.6 | 13.1 | 98.5 |
| I-4792 | 37.3 | 14.9 | 114.8 | 13.3 | 102.4 |
| Test 12: 35° C., 500 ppm N, pH 5 | | | | | |
| I-4072 | 31.6 | 16.5 | 117.4 | 14.7 | 1044 |
| I-4790 | 30.5 | 15.4 | 119.9 | 13.7 | 106.6 |
| I-4791 | 31.7 | 15.7 | 117.7 | 14.0 | 104.7 |
| I-4792 | 27.2 | 15.9 | 121.2 | 14.1 | 107.6 |
| Test 15: 38° C., 500 ppm N, pH 4 | | | | | |
| I-4072 | 82.7 | 14.1 | 87.7 | 12.9 | 80.2 |
| I-4790 | 80.3 | 13.1 | 85.8 | 11.9 | 78.4 |
| I-4791 | 80.9 | 12.9 | 88.1 | 11.8 | 80.5 |
| I-4792 | 82.7 | 13.5 | 86.4 | 123 | 78.9 |
| Test 14: 38° C., 500 ppm N, pH 5 | | | | | |
| I-4072 | 72.7 | 14.8 | 93.4 | 13.5 | 84.8 |
| I-4790 | 76.0 | 13.8 | 92.2 | 12.5 | 83.9 |
| I-4791 | 76.8 | 14.3 | 92.1 | 13.0 | 83.8 |
| I-4792 | 75.8 | 14.070 | 93.375 | 12.8 | 84.9 |

These results clearly show that the hybrids have a better tolerance to ethanol than the I-4072 starting strain (exhibiting an advantage of 2 to 3% over the I-4072 strain) and that they produce less glycerol than the I-4072 strain. This lower production of glycerol by the I-4790, I-4791 and I-4792 strains should logically lead to a better yield of conversion of the consumed sugars to ethanol.

Ethanol production kinetics. By way of example, the loss-of-mass kinetics of tests 10-13 are presented in FIG. 2.

These results show that the I-4072 strain has the fastest ethanol production kinetics of all the strains tested. Among the hybrids of the invention, the I-4791 hybrid has ethanol production kinetics that are more or less similar to those of the I-4072 strain. On the other hand, the I-4790 hybrid exhibits the slowest kinetics with delays ranging up to 10 hours at pH 5.

Example 5: Tests for Ethanol Production From Corn Flour by the Hybrids with Limiting Concentrations of Sugars in the Medium Yield of Conversion to Ethanol.

In order to reinforce the previous results, several tests were carried out with corn flour concentrations lower than those used in the tests of example 4 and such that the strains may totally consume the fermentable sugars of the medium. The tests carried out are given in the following table 5:

TABLE 5

| | Fermentation conditions | | | |
|---|---|---|---|---|
| | Test | | | |
| | 16 | 17 | 18 | 19 |
| Conditions | | | | |
| Medium | C | D | C | D |
| T (° C.) | 32 | 35 | 32 | 35 |
| N (ppm) | 250 | 250 | 150 | 150 |
| pH | 5 | 5 | 5 | 5 |
| Strains tested | | | | |
| I-4072 | x | x | x | x |
| I-4790 | x | x | x | x |

TABLE 5-continued

| | Fermentation conditions | | | |
|---|---|---|---|---|
| | Test | | | |
| | 16 | 17 | 18 | 19 |
| I-4791 | x | x | x | x |
| I-4792 | x | x | x | x |

C: 32° C.: 33% corn flour, 35% soluble materials from distillation residues, 32% process water
D: 35° C.: 30% corn flour, 35% soluble materials from distillation residues, 35% process water The results are presented in the following tables 6 and 7.

TABLE 6

| | Final concentrations (g/kg) | | | Mass produced (g/kg of medium used) | |
|---|---|---|---|---|---|
| Strain | Equiv. glucose | Glycerol | Ethanol | Glycerol | Ethanol |
| Test 16 32° C., 150 ppm N, pH 5 | | | | | |
| I-4072 | 1.6 | 16.9 | 118.7 | 8.3 | 105.3 |
| I-4790 | 1.6 | 15.9 | 122.3 | 7.4 | 108.6 |
| I-4791 | 1.8 | 17.1 | 121.9 | 8.5 | 108.2 |
| I-4792 | 1.9 | 16.5 | 119.8 | 7.9 | 106.4 |
| Test 17 35° C., 150 ppm N, pH 5 | | | | | |
| I-4072 | 1.5 | 16.1 | 102.4 | 7.7 | 91.7 |
| I-4790 | 1.4 | 14.7 | 107.9 | 6.5 | 96.6 |
| I-4791 | 1.5 | 15.1 | 108.1 | 6.8 | 96.6 |
| I-4792 | 1.4 | 15.0 | 109.6 | 6.7 | 97.9 |

TABLE 7

| | Final concentrations (g/kg) | | | Mass produced (g/kg of medium used) | |
|---|---|---|---|---|---|
| Strain | Equiv. glucose | Glycerol | Ethanol | Glycerol | Ethanol |
| Test 18 32° C., 250 ppm N, pH 5 | | | | | |
| I-4072 | 1.9 | 14.8 | 116.2 | 8.1 | 103.6 |
| I-4790 | 1.5 | 13.9 | 117.1 | 7.2 | 104.4 |
| I-4791 | 1.7 | 13.9 | 117.3 | 7.3 | 104.7 |
| I-4792 | 1.6 | 14.6 | 116.7 | 7.8 | 104.2 |
| Test 19 35° C., 250 ppm N, pH 5 | | | | | |
| I-4072 | 1.5 | 14.5 | 106.1 | 7.9 | 95.3 |
| I-4790 | 1.4 | 13.0 | 106.5 | 6.5 | 95.9 |
| I-4791 | 1.5 | 13.6 | 105.8 | 7.1 | 95.2 |
| I-4792 | 1.5 | 13.9 | 103.2 | 7.3 | 92.9 |

The results obtained confirm the observations made in the previous tests: the hybrids I-4790, I-4791 and I-4792 produce significantly less glycerol and more ethanol than the I-4072 reference strain, in particular at a reduced dose of provided nitrogen (N).

Conclusions. The results obtained clearly demonstrate that:
- the I-4791 hybrid has: ethanol production kinetics that are identical or similar to those of I-4072, a better tolerance to ethanol (+2%), a lower production of glycerol (−5%), and a better ethanol yield (+2%);
- the I-4790 hybrid has: a better tolerance to ethanol than I-4072 (+3%), a lower production of glycerol (−10%) and a better ethanol yield (+2%), but ethanol production kinetics that are slower than those of I-4072;
- the I-4792 hybrid has: a better tolerance to ethanol than I-4072 (+3%) except under harsh conditions (38° C./pH 4), ethanol production kinetics similar to those of I-4072, a lower production of glycerol (−5%) and a higher ethanol yield (+1%).

Example 6: Tests for Production of Yeasts From the Three Hybrids Selected

The hybrids selected were multiplied, on a pilot scale, under aerated conditions according to a fed-batch scheme well known to those skilled in the art. The yeasts obtained were dried according to the usual techniques. These yeast production tests took place without any particular problem being noted.

Ethanol production tests were carried out using the instant dry yeasts produced with the aim of verifying that the yeast production process does not impair the performance levels of the strains produced.

Protocol.

The fermentation media were prepared from corn flour, fractions of the soluble materials from distillation residues and process water. These various elements were obtained from industrial ethanol production factories. The proportions of the three industrial components were: corn flour (36% w/w), fraction of distillation soluble materials (35% w/w) and water (29% w/w). The mixture was liquefied using Liquozyme SCDS™ (Novozymes) at 85° C. for 3 hours after adjustment of the pH to 5.6. The Liquozyme™ dose used was 0.8 ml/kg of flour used.

The dry yeasts produced from the hybrids I-4790, 1-4791 and I-4792 and the commercial yeast Ethanol Red™ were propagated on the liquefied medium diluted in water (70% w/w, 30% w/w). The level of inoculation was 0.5 g of dry yeast/kg of medium, the pH was adjusted to 5, the propagation temperature was 32° C., and urea (500 ppm) and Spirizyme Fuel Ultra™ (0.6 ml/kg of flour) were added. The propagation medium was transferred to the fermentation medium with a transfer of 10% weight/weight.

The fermentations were carried out under the conditions described in table 8.

TABLE 8

| | | Tests | | | |
|---|---|---|---|---|---|
| | | 20 | 21 | 22 | 23 |
| | Conditions | | | | |
| Medium | | B | B | B | B |
| T (° C.) | | 32 | 35 | 32 | 35 |
| urea (ppm) | | 500 | 500 | 300 | 300 |
| initial pH | | 5 | 5 | 5 | 5 |
| Instant dry yeasts tested | | | | | |
| Ethanol Red ™ yeast | | x | x | x | x |
| I-4790 | Batch 1 | x | x | x | x |
| I-4790 | Batch 2 | x | x | x | X |
| I-4791 | Batch 1 | x | x | x | X |
| I-4791 | Batch 2 | X | x | x | x |
| I-4792 | Batch 1 | X | x | x | x |
| I-4792 | Batch 2 | x | x | x | X |

B: 36% corn flour, 35% soluble materials derived from distillation residues, 29% process water The results obtained, which are given in table 9, confirm, within the limit of the accuracy of the tests carried out, the results already obtained and confirm the possibility of producing and drying the I-4790, I-4791 and I-4792 strains.

Conclusions. The results obtained according to the invention made it possible to obtain industrial yeasts having performance levels that are significantly improved in terms of productivity and yield when they are used for the production of ethanol from sugars derived from plant biomasses.

Compared to the reference product on the market (Ethanol Red™):
- The 1-4790 industrial strain makes it possible to improve the ethanol productivity by +2% with an improved ethanol/sugar yield by virtue of the 10% reduction in the amount of glycerol generated;
- The I-4791 industrial strain makes it possible to improve the ethanol productivity by +2% with an improved ethanol/sugar yield by virtue of the 5% reduction in the amount of glycerol generated;
- The I-4792 industrial strain makes it possible to improve the ethanol productivity by +1% with an improved ethanol/sugar yield by virtue of the 5% reduction in the amount of glycerol generated.

TABLE 9

| Instant dry yeast | Batch | Final concentrations (g/kg) | | | Masses produced (g/kg of medium used) | |
|---|---|---|---|---|---|---|
| | | Glucose | Glycerol | Ethanol | Glycerol | Ethanol |
| 32° C., 300 ppm | | | | | | |
| Ethanol Red ™ | | 18.3 | 16.9 | 113.5 | 8.3 | 95.6 |
| I-4791 | 1 | 10.6 | 16.8 | 118.1 | 8.1 | 99.2 |
| I-4791 | 2 | 10.7 | 16.8 | 119.5 | 8.1 | 100.5 |
| I-4790 | 1 | 12.1 | 15.8 | 116.8 | 7.3 | 98.4 |
| I-4790 | 2 | 16.5 | 16.1 | 109.5 | 7.7 | 92.2 |
| I-4792 | 1 | 16.2 | 16.4 | 112.9 | 7.8 | 95.2 |
| I-4792 | 2 | 14.4 | 16.4 | 112.8 | 7.8 | 94.8 |
| 35° C., 300 ppm urea | | | | | | |
| Ethanol Red ™ | | 33.6 | 16.1 | 103.1 | 7.7 | 86.9 |
| I-4791 | 1 | 29.7 | 15.9 | 103.5 | 7.4 | 87.0 |
| I-4791 | 2 | 33.3 | 15.9 | 101.9 | 7.5 | 85.9 |
| I-4790 | 1 | 29.3 | 15.5 | 103.4 | 7.1 | 87.2 |
| I-4790 | 2 | 27.9 | 15.5 | 107.8 | 7.1 | 90.9 |
| I-4792 | 1 | 33.2 | 15.4 | 102.9 | 7.0 | 86.9 |
| I-4792 | 2 | 38.0 | 15.2 | 99.8 | 6.9 | 84.3 |
| 32° C., 500 ppm urea | | | | | | |
| Ethanol Red ™ | | 11.8 | 17.0 | 116.4 | 8.2 | 97.4 |
| I-4791 | 1 | 3.4 | 15.8 | 121.2 | 7.0 | 100.7 |
| I-4791 | 2 | 6.3 | 16.5 | 119.5 | 7.7 | 100.0 |
| I-4790 | 1 | 4.6 | 16.0 | 112.0 | 7.4 | 93.4 |
| I-4790 | 2 | 5.1 | 16.0 | 124.0 | 7.4 | 104.1 |
| I-4792 | 1 | 5.9 | 16.5 | 121.3 | 7.8 | 101.9 |
| I-4792 | 2 | 6.7 | 16.5 | 121.9 | 7.8 | 102.3 |
| 35° C., 500 ppm urea | | | | | | |
| Ethanol Red ™ | | 21.3 | 16.0 | 116.5 | 7.5 | 98.1 |
| I-4791 | 1 | 19.8 | 15.8 | 118.5 | 7.2 | 99.6 |
| I-4791 | 2 | 19.1 | 15.9 | 119.9 | 7.3 | 101.0 |
| I-4790 | 1 | 19.1 | 15.2 | 116.3 | 6.8 | 97.8 |
| I-4790 | 2 | 19.4 | 15.0 | 115.7 | 6.6 | 97.3 |
| I-4792 | 1 | 20.3 | 15.6 | 118.7 | 7.1 | 100.2 |
| I-4792 | 2 | 20.3 | 15.8 | 118.2 | 7.3 | 99.5 |

The invention claimed is:

1. A method for producing first-generation ethanol from biomass, comprising a step of fermenting biomass to ethanol using a *Saccharomyces cerevisiae* yeast strain chosen from the yeast strain deposited on Jul. 25, 2013, at the CNCM under number I-4791 and the yeast strain deposited on Jul. 25, 2013, at the CNCM under number I-4790, wherein said *Saccharomyces cerevisiae* yeast strain results from hybridization of the yeast strain deposited on Sep. 4, 2008 at the CNCM under number I-4072, and the yeast strain deposited on Jun. 26, 2013 at the CNCM under number I-4782, and wherein said *Saccharomyces cerevisiae* yeast strain exhibits a tolerance to ethanol that is higher than the tolerance to ethanol exhibited by the yeast strain deposited under number I-4072.

2. The method according to claim 1, wherein the biomass comprises sugar, or starch, or a mixture of sugar and starch.

3. The method according to claim 2, wherein the biomass comprises or originates from sugar cane, sugar beet, sweet sorghum, corn, wheat, barley, rye, sorghum, triticale, potato, sweet potato cassava, or a mixture thereof.

4. A method for producing first-generation ethanol from biomass, comprising a step of fermenting biomass to ethanol at a temperature of from 32° C. to 35° C. and a pH from 5 to 5.5 using a *Saccharomyces cerevisiae* yeast strain chosen from the yeast strain deposited on Jul. 25, 2013, at the CNCM under number I-4791, the yeast strain deposited on Jul. 25, 2013, at the CNCM under number I-4790, and the yeast strain deposited on Jul. 25, 2013, under number I-4792, wherein said *Saccharomyces cerevisiae* yeast strain results from hybridization of the yeast strain deposited on Sep. 4, 2008 at the CNCM under number I-4072, and the yeast strain deposited on Jun. 26, 2013 at the CNCM under number I-4782, and wherein said *Saccharomyces cerevisiae* yeast strain exhibits a tolerance to ethanol that is higher than the tolerance to ethanol exhibited by the yeast strain deposited under number I-4072.

5. The method according to claim 4, wherein the biomass comprises sugar, or starch, or a mixture of sugar and starch.

6. The method according to claim 4, wherein the biomass comprises or originates from sugar cane, sugar beet, sweet sorghum, corn, wheat, barley, rye, sorghum, triticale, potato, sweet potato cassava, or a mixture thereof.

* * * * *